United States Patent
Park et al.

(10) Patent No.: US 12,226,773 B2
(45) Date of Patent: Feb. 18, 2025

(54) METHOD AND DEVICE FOR ENCAPSULATING CELL IN LIQUID DROPLET FOR SINGLE-CELL ANALYSIS

(71) Applicant: Samsung Life Public Welfare Foundation, Seoul (KR)

(72) Inventors: Woong-Yang Park, Seoul (KR); Hui-Sung Moon, Gyeonggi-do (KR); Shin-Hyun Kim, Daejeon (KR); Kwanghwi Je, Daejeon (KR)

(73) Assignee: SAMSUNG LIFE PUBLIC WELFARE FOUNDATION, Seoul (KR)

( * ) Notice: Subject to any disclaimer, the term of this patent is extended or adjusted under 35 U.S.C. 154(b) by 193 days.

(21) Appl. No.: 17/962,752

(22) Filed: Oct. 10, 2022

(65) Prior Publication Data
US 2023/0030813 A1   Feb. 2, 2023

Related U.S. Application Data

(60) Division of application No. 16/686,613, filed on Nov. 18, 2019, now abandoned, which is a
(Continued)

(30) Foreign Application Priority Data

May 17, 2017   (KR) ........................ 10-2017-0061053

(51) Int. Cl.
*C12Q 1/6869* (2018.01)
*B01L 3/00* (2006.01)

(52) U.S. Cl.
CPC ... *B01L 3/502761* (2013.01); *B01L 3/502776* (2013.01); *B01L 3/502784* (2013.01);
(Continued)

(58) Field of Classification Search
CPC ..... B01L 2200/0636; B01L 2200/0652; C12Q 1/6869; C12Q 2525/185; C12Q 2563/149;
(Continued)

(56) References Cited

U.S. PATENT DOCUMENTS

| | | |
|---|---|---|
| 2011/0223314 A1 | 9/2011 | Zhang et al. |
| 2015/0355096 A1 | 12/2015 | Natale |
| 2017/0128940 A1 | 5/2017 | Amini |

FOREIGN PATENT DOCUMENTS

| | | | | |
|---|---|---|---|---|
| WO | WO-2015200717 A2 | * | 12/2015 | ............. C12Q 1/686 |
| WO | WO-2016040476 A1 | * | 3/2016 | ......... C12N 15/1096 |

(Continued)

OTHER PUBLICATIONS

Xue, Chundong et al.: "Lateral migration of dual droplet trains in a double spiral microchannel", *Science China Physics, Mechanics & Astronomy*, Jul. 2016, vol. 59, No. 7, 674711, pp. 1-10.
(Continued)

*Primary Examiner* — Joseph G. Dauner
(74) *Attorney, Agent, or Firm* — Panitch Schwarze Belisario & Nadel LLP

(57) ABSTRACT

Provided are a method and a device for encapsulating a cell in droplet for single-cell analysis, or a method and a device for forming droplet for single-cell analysis. According to the method and the device of one aspect, by using the effects of inertial ordering, not only a ratio at which one cell is encapsulated in one droplet is increased, but also a yield of generating droplet is improved.

5 Claims, 18 Drawing Sheets

Related U.S. Application Data continuation-in-part of application No. PCT/KR2018/005646, filed on May 17, 2018.

(52) U.S. Cl.
CPC .... *C12Q 1/6869* (2013.01); *B01L 2200/0636* (2013.01); *B01L 2200/0652* (2013.01); *B01L 2300/0867* (2013.01)

(58) Field of Classification Search
CPC ........ C12Q 2563/159; C12Q 2563/179; C12Q 2565/629; C12Q 1/6806
See application file for complete search history.

(56) References Cited

FOREIGN PATENT DOCUMENTS

| WO | WO-2017046565 | A1 | * | 3/2017 | ............ | B01L 3/0241 |
|----|---------------|----|---|--------|--------------|-------------|
| WO | WO-2017048975 | A1 | * | 3/2017 | ........ | B01L 3/502761 |
| WO | WO-2017053902 | A1 | * | 3/2017 | .............. | A61P 35/00 |
| WO | WO-2017066231 | A1 | * | 4/2017 | ........... | A61K 47/549 |

OTHER PUBLICATIONS

Moon, Hui-Sung et al.: "Inertial-ordering-assisted Droplet Microfluidies for High-throughput Single-cell RNA-sequencing", Lab on a Chip, Jan. 31, 2018, vol. 18, No. 5, pp. 775-784.

International Search Report and Written Opinion prepared by the Korean Intellectual Property Office, acting as The International Search Authority for priority international application PCT/KR2018/005646 mailed Aug. 14, 2018.

Li et al. Dean Flow Assisted Single Cell and Bead Encapsulation for High Performance Single Cell Expression Profiling (2019) ACS Sens. 4, 1299-1305 (2019).

* cited by examiner

METHOD AND DEVICE FOR ENCAPSULATING CELL IN LIQUID DROPLET FOR SINGLE-CELL ANALYSIS

CROSS-REFERENCE TO RELATED APPLICATIONS

This application is a Divisional Application of U.S. patent application Ser. No. 16/686,613, filed on Nov. 18, 2019, which is a Continuation-in-part of International Patent Application PCT/KR2018/005646, filed on May 17, 2018, and which claims priority to Korean Patent Application 10-2017-0061053, filed on May 17, 2017, all of which are incorporated herein by reference in their entireties for all purposes.

TECHNICAL FIELD

The present disclosure relates to a method and a device for encapsulating a cell in droplet for single-cell analysis, or a method and a device for forming droplet for single-cell analysis.

BACKGROUND ART

Cell analysis using microfluids may be utilized particularly for single-cell genome analysis. Genetic heterogeneity, which occurs at a single-cell level in cancer, is an important clue for precise diagnosis and prognosis prediction of cancer, and in this regard, the importance of single-cell analysis is significantly increasing. The single-cell analysis may be applied to many studies associated with not only cancer, but also identification of cells made of IPS cells or stem cells and subtype analysis of cell bodies.

To perform such single-cell analysis, a step of independently reacting individual cells is carried out by isolation and compartmentalization of cells into a single-cell unit before experiment. Techniques of isolation and compartmentalization into single cells largely include a method of putting one cell into one well by using a valve and a micro-well and a method of putting one cell into one water droplet in oil by using emulsion. The latter method using emulsion has advantages of enabling encapsulation of a cell and a particle in droplet, resulting in fast, accurate, and efficient genome analysis of single cells. In particular, as shown in FIG. 1, single-cell RNA sequencing analyzes a base sequence through processes of dissolving single cells to extract RNA therefrom, producing cDNA by reverse transcription, and preparing a standardized sequencing after amplification of the cDNA. Considering that processes associated with each one of the single cells would cause a lot of time, labor, and cost, a method of indexing single cell-originated RNA with a single barcode and pooling the indexed RNA at a step of reverse transcription or amplification to proceed the next step is recently used.

However, in a microfluidic device for single-cell analysis, a process that a cell and a particle are met and encapsulated continuously occurs. Here, such a cell and a particle enter a device in a random distribution state, and an encapsulation phenomenon is also influenced by distribution of the cell and the bead. When the inter-cell distance or the inter-particle distance is too narrow, the probability of entering two or more clusters increases. In addition, when concentrations of the cell and the bead decrease, the cell and the bead are less likely to form droplet, resulting in lower efficiency (yield) of producing droplet. Therefore, there is a need for a technique for enhancing the efficiency of the two conflicting parameters described above.

DESCRIPTION OF EMBODIMENTS

Technical Problem

The present disclosure provides a method and a device for encapsulating a cell in droplet for single-cell analysis, so as to improve the two conflicting parameters described above, in terms of single-cell analysis for droplet sequencing.

Solution to Problem

To achieve the object above, the present disclosure provides a method of forming droplet for single-cell analysis, the method including: providing cells; providing one or more distinctly barcoded RNA capture beads; and encapsulating in one droplet a single cell of the cells and a single bead of the one or more distinctly barcoded RNA capture beads, wherein the providing of the cells or the providing of the one or more distinctly barcoded RNA capture beads is provided through inertial ordering before the single cell or the single bead are encapsulated in the one droplet.

The inertial ordering may occur through a spiral channel of a microfluidic device to which the cells or the one or more distinctly barcoded RNA capture beads are provided.

In addition, the method may further include providing one or more oils (carrier oils).

In addition, the inertial ordering may be to improve a ratio at which the single cell and the single bead are encapsulated in the one droplet.

In addition, the providing of the cells or the providing of the cells or the one or more distinctly barcoded RNA capture beads may be provided at a flow rate of at least 1.0 ml/h or higher.

In addition, the providing of the one or more carrier oils may be provided at a flow rate of at least 2 ml/h or higher.

In addition, the one or more distinctly barcoded RNA capture beads may be provided in a cell lysate or with a cell lysate.

In addition, the one or more distinctly barcoded RNA capture beads may include multiple nucleotides or oligonucleotides, each molecularly barcoded on a surface of the one or more distinctly barcoded RNA capture beads.

In addition, the multiple nucleotides or oligonucleotides may include a nucleotide sequence for capturing mRNA in the cells.

In addition, a sequence of the multiple nucleotides or oligonucleotides may include an oligo-dT sequence or a primer sequence.

Another aspect of the present disclosure provides a microfluidic device for forming droplet for single-cell analysis, including: a cell inlet including a first channel; an RNA capture bead inlet including a second channel; an oil phase inlet including a third channel; an intersection point at which the first channel, the second channel, and the third channel are combined; and an outlet connected to the intersection point and discharging droplet containing the cells and R NA containing a cell and an RNA capture bead, wherein the first channel or the second channel is configured for a cell or an RNA capture bead in a fluid to occur inertial ordering.

In addition, the first channel and/or the second channel may be spiral shaped.

In addition, the cell inlet, the RNA capture bead inlet, or the oil phase inter may further include a filter.

ADVANTAGEOUS EFFECTS OF DISCLOSURE

According to a method and a device for encapsulating a cell in droplet, or a method and a device for forming droplet for single-cell analysis of one aspect, effects of using inertial ordering may not only increase a ratio at which one cell is encapsulated in one droplet, but also improve a yield of producing droplet.

MODE OF DISCLOSURE

Figure 1:
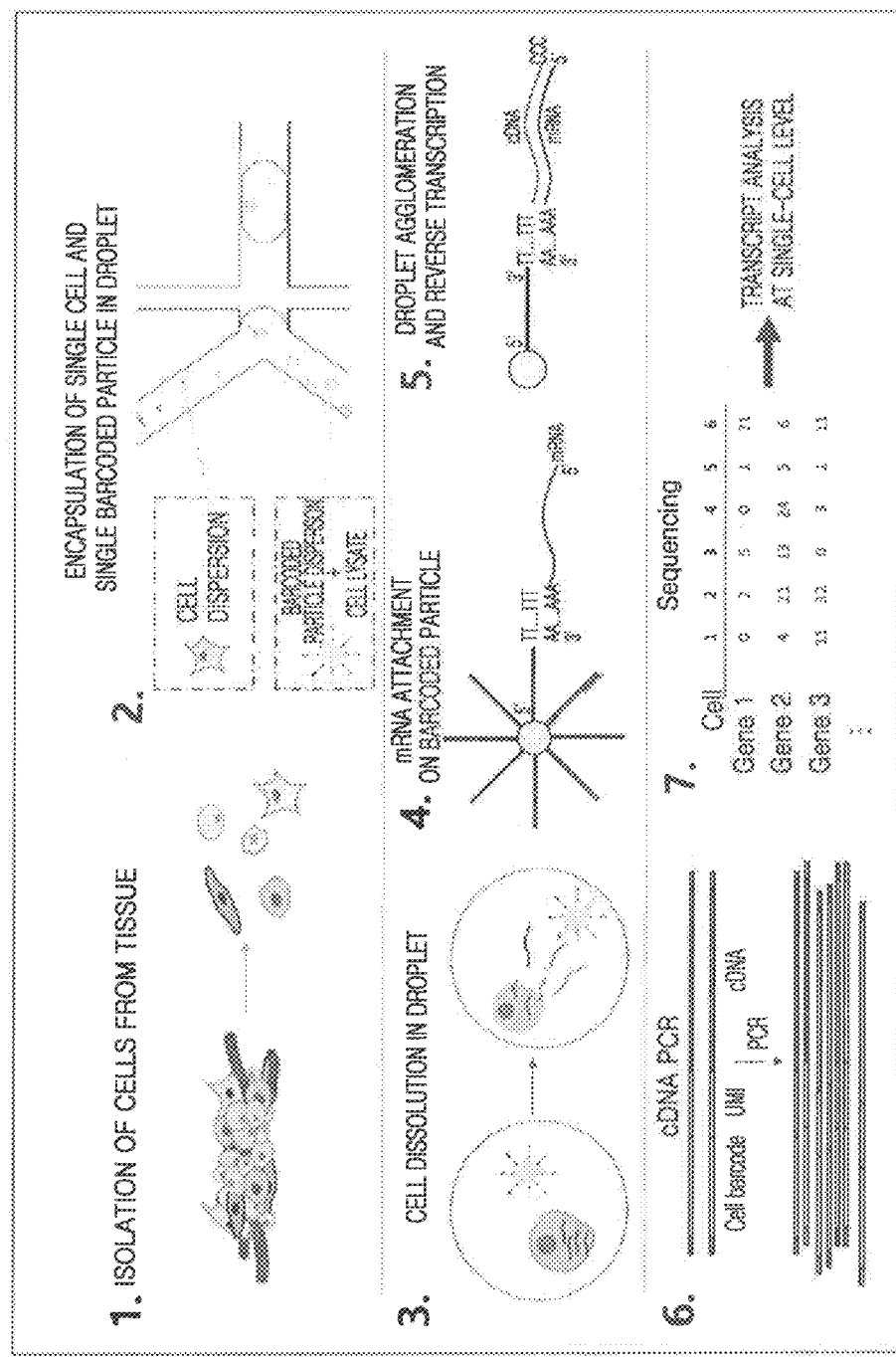
FIG. 1 is a diagram illustrating the principle of droplet sequencing.

An aspect provides a method of forming droplet for single-cell analysis, the method including: providing cells; providing one or more distinctly barcoded RNA capture beads; and encapsulating in one droplet a single cell of the provided cells and a single bead of the one or more distinctly barcoded RNA capture beads, wherein the providing of the cells or the providing of the one or more distinctly barcoded RNA capture beads is provided through inertial ordering before the single cell and the single bead are encapsulated in the one droplet.

The term "droplet" as used herein refers to a small volume of liquid, typically in a spherical shape, surrounded by an immiscible fluid such as a continuous phase of emulsion. Among droplet, "micro-droplet" may have a value of about 1 microliter or less, for example, a value between about 1 microliter and about 1 nanoliter, or a value between about 1 microliter and about 1 picoliter. Alternatively, micro-droplet may refer to a dispersed phase having a diameter of less than about 200 micrometers.

The term "carrier fluid" as used herein is used interchangeably with "carrier oil", and may refer to any liquid compound or a mixture thereof that is immiscible with water (or aqueous solution).

The term "sample" as used herein is not particularly limited as long as it contains a specimen to be detected. For example, a sample may be a biological sample, such as a biological fluid or a biological tissue. Examples of the biological fluid include urine, blood, plasma, serum, saliva, semen, feces, sputum, cerebrospinal fluid, tears, mucus, amniotic fluid, and the like. The biological tissue refers to a collection of cells, and typically, may be a collection of certain types of intracellular substances that form one of structural substances of human, animal, plant, bacterial, fungal, or viral structures. Examples of the biological tissue include a connective tissue, an epithelial tissue, a muscle tissue, a neural tissue, and the like. In addition, as examples of the biological tissue, an organ, a tumor, a lymph node, artery, and an individual cell(s) may be included.

The term "reagent" as used herein refers to a compound or a set thereof, and/or a composition, which is bound to a sample to perform a specific test on the sample. For example, the reaction reagent may be an amplification reagent, specifically, a primer for amplifying a target nucleic acid, a probe and/or a dye for detecting an amplified product, a polymerase, a nucleotide (e.g., dNTP), a magnesium ion, a potassium chloride, a buffer, or any combination thereof. In the present specification, the reagent reagent may include a distinctly barcoded particle (e.g., a bead). Such a bead may include multiple nucleotides or oligonucleotides that are molecularly barcoded on a surface of the bead. In addition, the multiple nucleotides or oligonucleotides may include a nucleotide sequence for capturing mRNA in the cells. In addition, a sequence of the multiple nucleotides or oligonucleotides may include an oligo-dT sequence or a primer sequence. In addition, the bead may be provided in a cell lysate or with a cell lysate.

The term "amplification" as used herein may refer to a reaction that occurs repeatedly to form multiple copies of at least one segment of a template molecule.

The term "PCR" as used herein refers to a reaction resulting in the formation of a large number of identical DNA strands from one original template by a cyclic process (alternative processes of heating and cooling). The PCR consists of (i) a double helix DNA molecule that is a template having a base sequence to be amplified, (ii) a primer (a single-stranded DNA molecule capable of binding to a complementary DNA sequence in the template DNA), (iii) dNTP which is a mixture (i.e., a nucleotide subunit that is combined to form a new DNA molecule during PCR amplification) of dATP, dTTP, dGTP, and dCTP, and (iv) a Taq DNA polymerase (i.e., an enzyme for synthesizing a new DNA molecule by using dNTP).

The term "complementary" as used herein refers that a base pair between nucleotides or nucleic acids can be hybridized, and is typically associated with a pair of A and T (or U) or a pair of C and G.

The term "channel" as used herein refers to a passageway through which a fluid flows, and for example, may be formed in a tube (e.g., capillary), in a planar structure, on a planar structure (e.g., chip), or a combination thereof. Such a channel in the present specification may be a channel extending along a planar flow path (e.g., a channel in a serpentine or spiral planar pattern) or a non-planar flow path (e.g., a three-dimensional spiral channel). That is, the inertial ordering may appear through a spiral channel of a microfluidic device to which the cells or the beads are provided. The channel may have a spiral of at least two loops, at least three loops, or at least 5 loops, for example, between 2 loops and 20 loops, or between 5 loops and 15 loops.

In one embodiment, the fluid flow within a microfluic channel may exhibit a poiseuille flow pattern, and when microparticles are present therein, a shear gradient lift force and a wall effect force that occurs at the channel walls are caused. Due to the interaction between the two forces applied on a particle, particles may be collected at a specific location, which is called inertia concentration. Here, the presence of particles may result in, in addition to the intensive movement of particles, a secondary flow that is formed by a change of the fluid flow, which can be seen as a force that pushes other particles or fluid around the particles. Such a force is known to occur when the space, such as the microchannel, is limited or when the inertia of the fluid is applied. Particles pushed out by this repulsive force are arranged at specific intervals, and such an arrangement is called inertial ordering. The spiral channel can amplify the effect of the inertial ordering by using Dean flow. Therefore, as the inertial ordering is caused in the present disclosure, the ratio at which one cell and one bead are encapsulated in one droplet is improved, thereby improving a yield in which the droplet is produced.

As Examples allows for various changes, particular Examples will be illustrated in the drawings and described in detail in the written description. Effects and characteristics of Examples, and methods of achieving the same will be apparent with reference to the following detailed description in connection with the drawings.

However, Examples may be embodied in many different forms and should not be construed as limited to the Examples set forth herein.

Hereinafter, Examples will be described more fully with reference to the accompanying drawings. Here, the same or corresponding elements will be denoted by the same reference numerals in the drawings, and redundant description thereof will be omitted.

It will be understood that although the terms "first," "second," etc. may be used herein to describe various components, these components should not be limited by these terms. These components are only used to distinguish one component from another.

As used herein, the singular forms "a," "an" and "the" are intended to include the plural forms as well, unless the context clearly indicates otherwise.

It will be further understood that the terms "comprises" and/or "comprising" used herein specify the presence of stated features or components, but do not preclude the presence or addition of one or more other features or components.

Sizes of components in the drawings may be exaggerated for convenience of explanation. In other words, since sizes and thicknesses of components in the drawings are arbitrarily illustrated for convenience of explanation, the following embodiments are not limited thereto.

Figure 3:
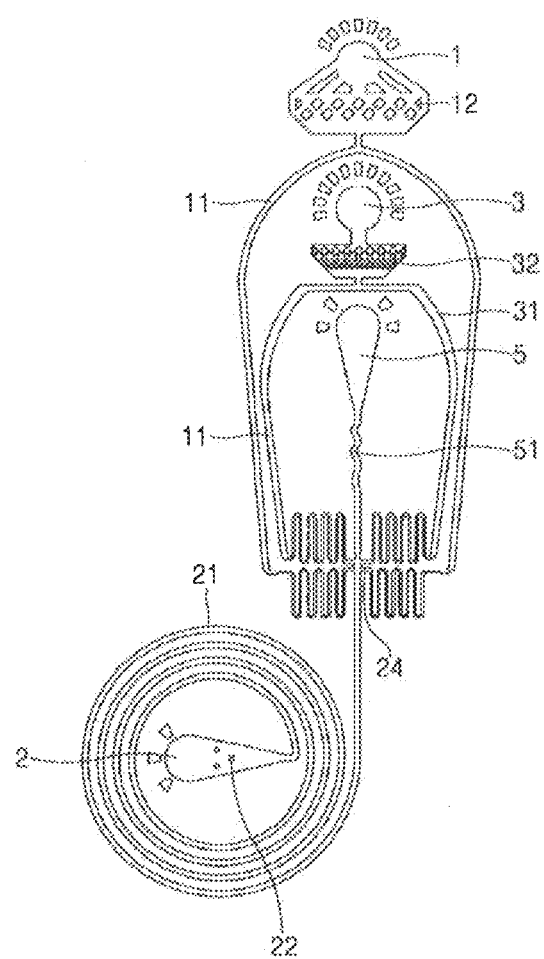
FIG. 3 is a diagram showing a droplet-forming microfluidic device according to an embodiment in which inertial ordering occurs at a bead inlet.

Referring to FIG. 3, a microfluidic device for forming droplet for single-cell analysis according to an embodiment includes: a cell inlet 1 including a first channel 11; a bead inlet 2 including a second channel 21; an oil phase inlet 3 including a third channel 31; an intersection point 4 in which the first channel 11, the second channel 21, and the third channel 31 are combined; and an outlet 5 connected to the intersection point 4 and discharging droplet including a cell and a bead.

Figure 2:
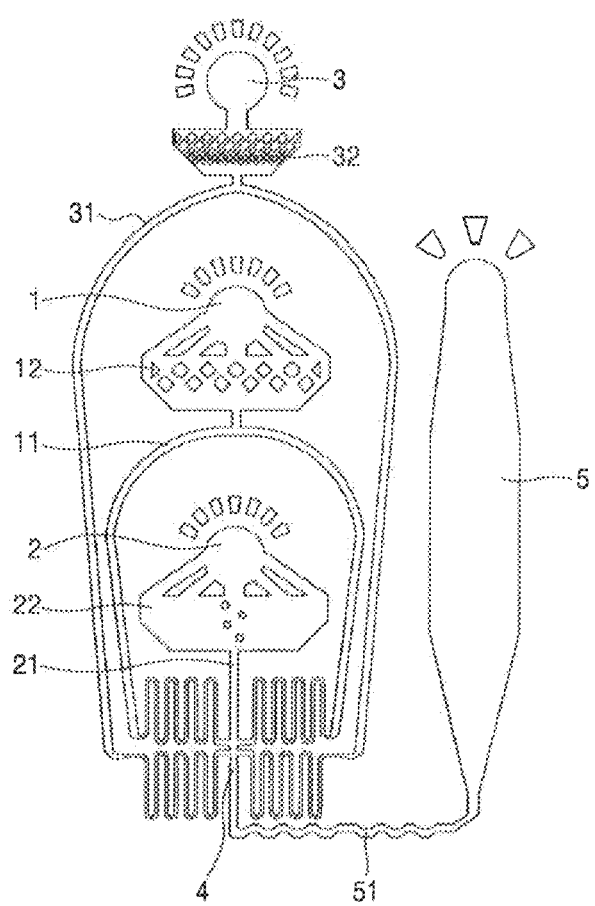
FIG. 2 is a diagram showing a droplet-forming microfluidic device in the related art.

In comparison with a microfluidic device of the related art as shown in FIG. 2, the microfluidic device of FIG. 3 may be configured to occur inertial ordering of cells or beads in the first channel 11 or the second channel 21. That is, the first channel 11 and/or the second channel may be in a spiral form. As such, by occurring the inertial ordering of cells or beads in the first channel 11 and/or the second channel 21, the microfluidic device according to an embodiment may not only improve the ratio at which one cell and one bead are encapsulated in one droplet, but also increase an output of droplet.

An aqueous state of the first channel 11 and/or the second channel 21 may have a flow rate of at least 1.0 ml/h or more, at least 1.6 ml/h or more, at least 2.0 ml/h or more, at least 2.4 ml/h or more, at least 2.8 ml/h or more, at least 3.0 ml/h or more, or at least 3.2 ml/h or more. In more detail, the flow rate of the aqueous phase may be in a range of 1.0 ml/h to 20 ml/h, 2.0 m/h to 20 ml/h, 3.0 ml/h to 20 ml/h, 2.0 ml/h to 16 m/h, 2.0 ml/h to 14 ml/h, 3.0 ml/h to 14 ml/h, or 3.2 ml/h to 14 ml/h.

In addition, an oil phase of the third channel 31 may have a flow rate of at least 2 ml/h or more, at least 4 ml/h or more, at least 6 ml/h or more, at least 8 ml/h or more, at least 10 ml/h or more, or at least 12 ml/h or more. In more detail, the flow rate of the oil phase may be in a range of 2.0 ml/h to 30 ml/h, 4.0 ml/h to 30 ml/h, 6.0 ml/h to 28 ml/h, 6.0 ml/h to 24 ml/h, 8.0 ml/h to 24 ml/h, 10 ml/h to 24 ml/h, or 12 ml/h to 24 ml/h.

In one embodiment, a flow rate is an important factor in achieving effects of the present disclosure. In particular, the flow rate of the oil phase is a significant factor in terms of the droplet-generation frequency. The frequency increases with increasing flow rate of the oil phase, and in particular, may be preferably in a range of 4.0 ml/h to 18 ml/h, 4.0 m/h to 10 ml/h, 4.0 ml/h to 8.0 ml/h, 6.0 ml/h to 8.0 ml/h, or 6.0 ml/h to 10 ml/h. In addition, the flow rate of the aqueous phase in combination with the flow rate of the above-mentioned oil phase may be in a range of 3.0 ml/h to 14 ml/h, 4.0 ml/h to 14 ml/h, 5.0 m/h to 14 ml/h, or 6.0 ml/h to 14 ml/h. Therefore, a combination of the flow rate of the oil phase in a range of 4.0 m/h to 10 ml/h or 4.0 ml/h to 8.0 ml/h and the flow rate of the aqueous phase in a range of 5.0 m/h to 14 ml/h or 6.0 ml/h to 14 mV/h, or a combination of the aforementioned flow rate ranges may be an optimal combination. Within the aforementioned flow rate, the droplet-generation frequency may be in a range of 1,000 Hz to 8,000 Hz, 1,000 Hz to 6,000 Hz, 2,000 Hz to 6,000 or 2,000 Hz to 4,000 Hz. In addition, at the flow rate of the aforementioned combination, stable dripping and jetting modes may be achieved.

In one embodiment, a width of the first or second channel to induce inertial ordering may be in a range of 30 to 500 um, 50 to 400 um, 60 to 300 um, 60 to 250 um, or 80 to 160 um.

In one embodiment, a height of the first or second channel to induce inertial ordering may be in a range of 30 to 500 um, 30 to 400 um, 50 to 300 um, 60 to 200 um, or 60 to 150 um.

In one embodiment, a Reynolds number to induce inertial ordering may be at least 8.5, for example, in a range of 1 to 40, 8 to 40, 8.5 to 40, or 8.5 to 30.

In one embodiment, a Dean number to induce inertial ordering may be at least 1.53, for example, in a range of 0.8 to 8, 1 to 8, 1.53 to 8, or 1.53 to 4.

In one embodiment, a Particle Reynolds number to induce inertial ordering may be at least 0.62, for example, in a range of 0.3 to 3, 0.5 to 3, 0.62 to 3, or 0.62 to 1.

The cells, the beads, the oil phase, and the droplet may each be understood by referring to descriptions thereof provided herein.

In addition, the cell inlet 1, each of the bead inlet 2, and the oil phase inlet 3 may further include a filter 12, 22, 32, respectively. The filter may include square PDMS posts.

In addition, the outlet 5 may further include a mixing unit 51 for better mixing of cells and beads formed in the droplet.

Figure 4:
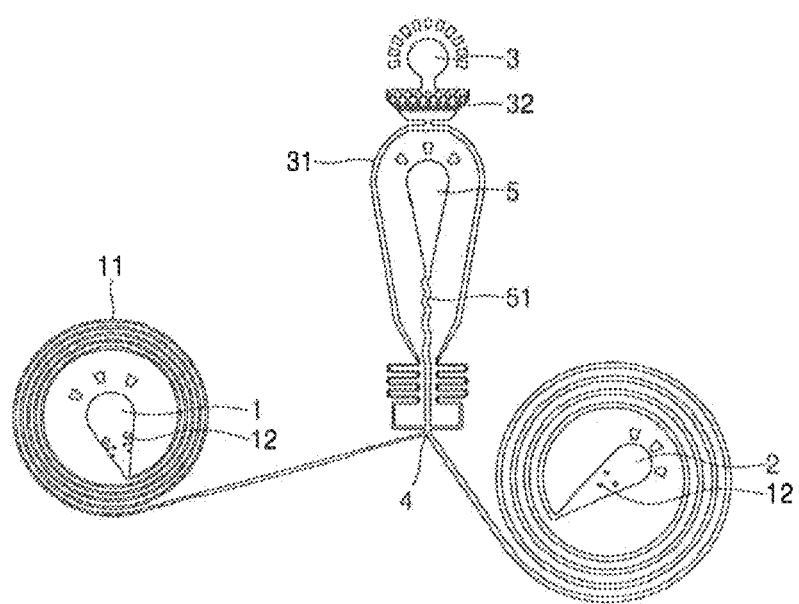
FIG. 4 is a diagram showing a droplet-forming microfluidic device according to an embodiment in which inertial ordering occurs at both a bead inlet and a cell inlet.

Referring to FIG. 4, one of or both the first channel 11 and the second channel 12 in the microfluidic device according to an embodiment may be in a spiral form.

In one embodiment, target cells may be introduced into the microfluidic device through the cell inlet 1, RNA of the introduced cells may be indexed through the bead inlet 2, and beads attached with oligonucleotides for capturing mRNA may be introduced into the microfluidic device. In addition, oil may be introduced into the microfluidic device through the oil inlet 3. The cells, the beads, and the oil that are introduced in this way are met at the intersection point 4 via the first channel 11, the second channel 21, and the third channel 31, and then, droplets may be formed near the intersection point 4. The formed droplets may be discharged through the outlet 5 via the mixing unit 51, and then, a process for subsequent sequencing analysis or the like may be performed thereon.

Example. Analysis of Inertial Ordering Using Spiral Channel and Effects Thereof

Effects of an existing microfluidic device as shown in FIG. 2 and a microfluidic device according to an embodiment as shown in FIG. 3 are compared and analyzed.

In detail, for use as cells, K562 cells (human), 293T cells (human), and NIH/3T3 cells (mouse) were used. To perform droplet sequencing, the cells were cultured in a RMPI-1640 medium (supplemented with 10% FBS, 2 mM glutamine, and 1% PS), and the cells contained in PBS were used in this experiment. In addition, as RNA capture beads barcoded to distinguish individual cells barcoded beads (#MACOSKO-2011-10) with a PCR handle, 12-based cell barcode, 8-based unique molecular identifier (UMI), and poly T site were purchased from manufactured from Chemgene Company. They were washed with ethanol and TE/TW (10 mM Tris pH 8.0, 1 mM EDTA, 0.01% Tween), and then, re-suspended in cell lysate and passed through a 100 μm filter (BD Falcon #352360) for the experiment. For the droplet sequencing, beads at a concentration of 500 beads/ul, 1,000 beads/ul, and 1,500 beads/ul were may be used. For use as the cell lysate, a mixed solution containing 200 mM Tris, pH 7.5, 20 mM EDTA, 6% Ficoll PM400, 0.2% Sarcosyl, and 50 mM DTT was used, and the beads were contained in the cell lysate. For use as the oil phase, Droplet Generation Oil (Biorad #186-4006) was used. A syringe pump had a rate of 14,000 ul/hr with oil and a rate of 4,100 ul/hr with the beads and the cells, and collected formed droplets in a falcon tube. In detail, the cell suspension, bead suspension, and droplet generation oil were injected into a microfluidic device through three main inlets using syringe pumps (Lagato 210, KD Scientific, Holliston, MA, USA). During injection, the cells and beads were continuously stirred in syringes by gentle magnetic mixing. In the microfluidic device, the cells and beads were co-encapsulated into 100 μm-diameter droplets. To optimize the flow conditions, serial images were captured at the spiral microchannel and channel junction with a high-speed camera (Phantom V7.3, Vision Research, Wayne, NJ, USA) equipped with an optical microscope (Ti—U, Nikon, Tokyo). Here, inertial ordering, bead-entering frequency, and droplet generation modes were characterized while varying the flow rates. The images were typically acquired at 5,000-10,000 frames per second. The produced droplets were collected in tubes, and then, loaded onto a dish. The occupancy of cells and beads in the droplets was evaluated by observing aliquots of droplets under an optical microscope (Ti—U, Nikon) and a fluorescence microscope (X81, Olympus, Tokyo, Japan).

(1) Inertial Ordering Using Spiral Channels

The alignment effect of particles (beads) in the channel of the existing microfluidic device of FIG. 1 and the microfluidic device of FIG. 3 according to an embodiment of the present disclosure was compared. In the following experiment, a microfluidic device according to an embodiment of the present disclosure is the microfluidic device of FIG. 3. In detail, the existing microfluidic device constituted a channel through which beads move as shown in FIG. 2, whereas the microfluidic device according to the present disclosure constituted a channel through which beads move as shown in FIG. 3. Then, the alignment of beads in each channel was observed, and results thereof are shown in FIGS. 5A and 5B.

Figure 5A:
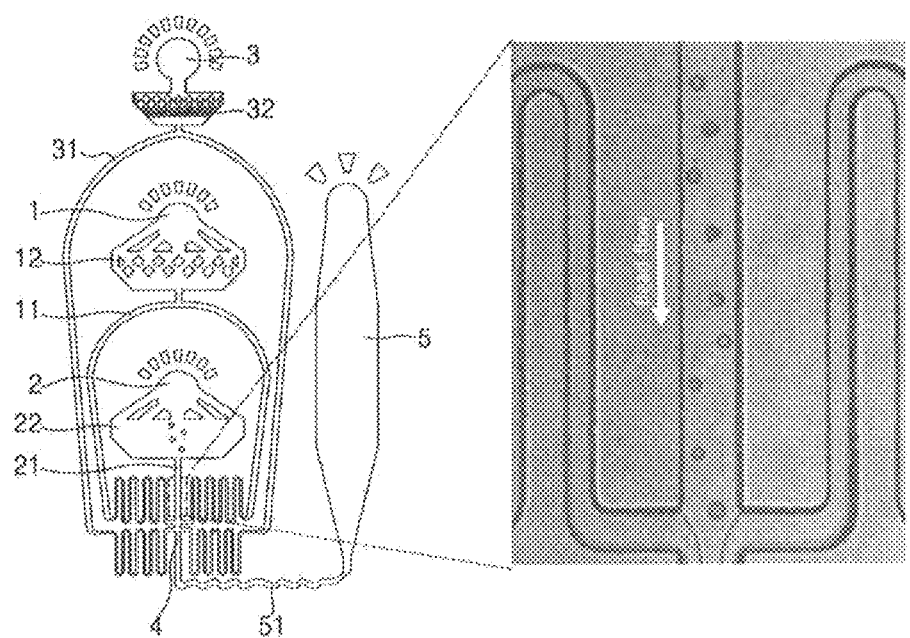
FIG. 5A is a photograph showing the alignment of particles using a microfluidic device in the related art.

FIG. 5A is a photograph showing the alignment of particles using the existing microfluidic device.

Figure 5B:
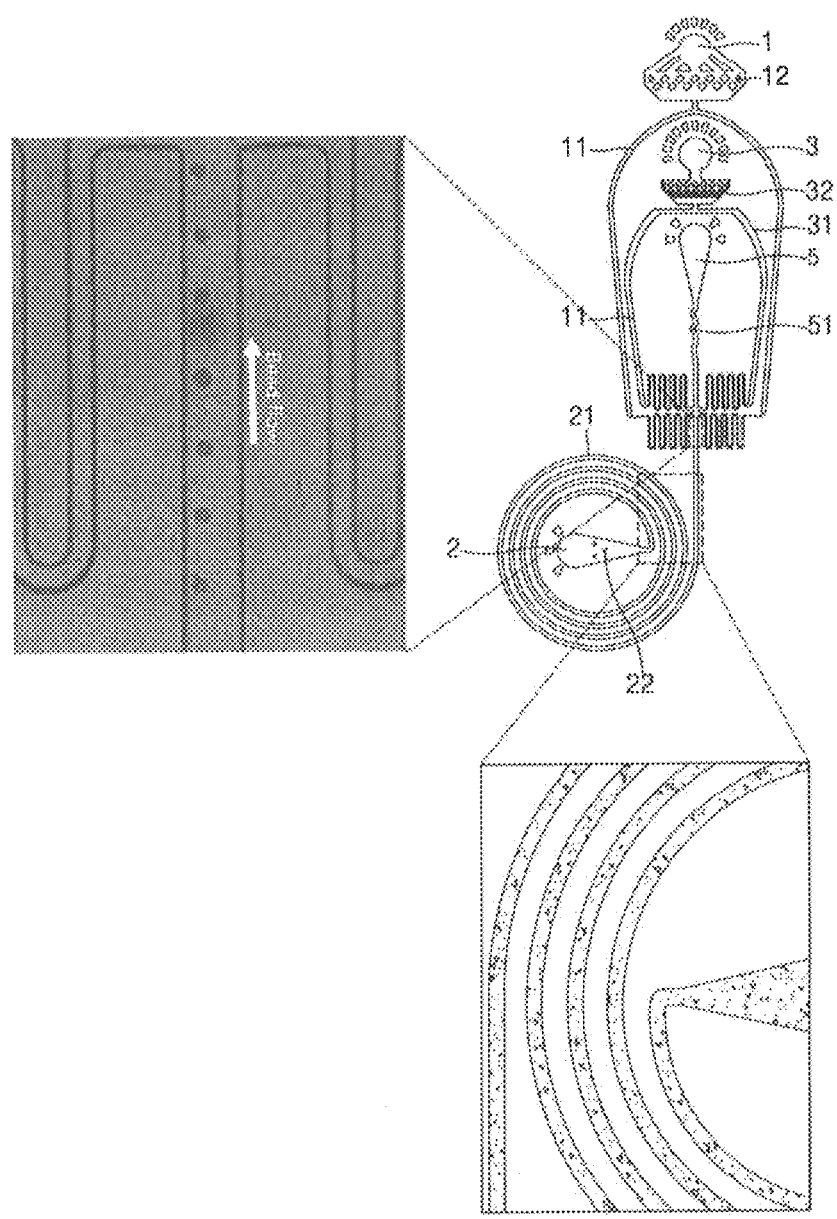
FIG. 5B is a photograph showing the alignment of particles using a microfluidic device according to an embodiment.

FIG. 5B shows the alignment of particles using the microfluidic device according to an embodiment of the present disclosure.

As shown in FIG. 5A, it was confirmed that the behavior of particles in the existing microfluidic device was not made smoothly in a way that the particles were agglomerated or clogged. On the contrary, as shown in FIG. 5B, the microfluidic device according to an embodiment of the present disclosure constitutes a channel in a spiral form, and accordingly, it was confirmed that the behavior of particles in the microfluidic device was made smoothly compared to the existing microfluidic device.

(2) Analysis of Ratio of Encapsulated Cells and Cell Throughput Per Hour Using Spiral Channels The cell throughput per hour and the ratio of cells encapsulated in droplets in the aforementioned existing microfluidic device and the microfluidic device according to an embodiment of the present disclosure were analyzed according to the concentration of beads. In detail, the existing system used beads at the concentration of 500 beads/ul, 1,000 beads/ul, and 1,500 beads/ul, whereas the system according to an embodiment of the present disclosure used beads at the concentration of 1,500 beads/ul. The cell yield indicates a ratio at which one cell and one bead are encapsulated in one droplet, and the cell throughput indicates the number of cells encapsulated per unit time. The results of the analysis are shown in FIGS. 6 and 7.

Figure 6:
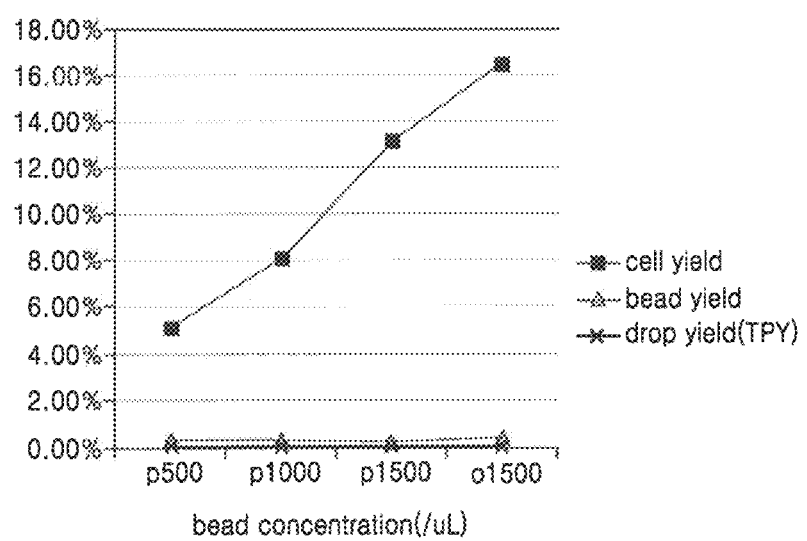
FIG. 6 is a graph showing a cell throughput per time and a cell yield per time according to the bead concentration in a microfluidic device according to an embodiment, as compared to an existing system, wherein p indicates an existing system, and o indicates a system according to an embodiment.

FIG. 6 is a graph showing the cell throughput per time and the cell yield per time according to the bead concentration in the microfluidic device according to an embodiment of the present disclosure as compared to the existing system, wherein p indicates the existing system, and o indicates the system according to an embodiment of the present disclosure.

As shown in FIG. 6, as the bead concentration increased, the existing system included more double or multi-cells in which two or more cells were encapsulated in one droplet, and accordingly, it was confirmed that the existing system has no choice but to maintain a low concentration. On the contrary, since the system according to an embodiment of the present disclosure used the inertial ordering, particles and cells at a high concentration could be introduced, and accordingly, it was confirmed that the cell yield was also able to be significantly increased.

Figure 7:
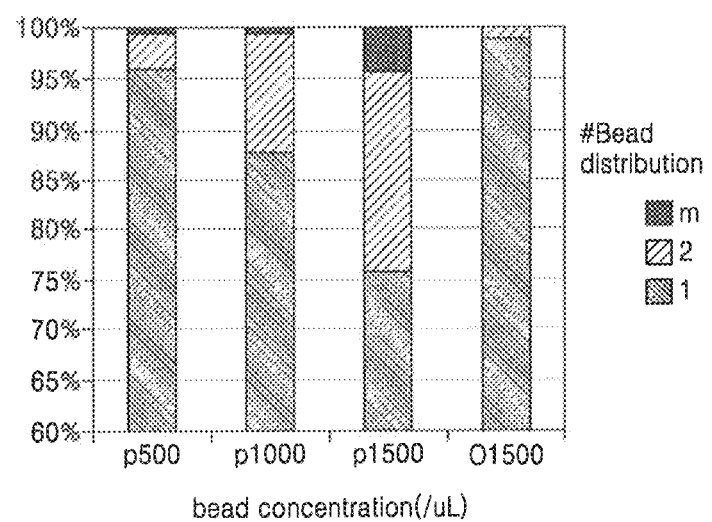
FIG. 7 is a graph showing a ratio of the number of cells to be encapsulated in droplet according to the bead concentration in a microfluidic device according to an embodiment, as compared to an existing system, wherein p indicates an existing system, o indicates a system according to an embodiment, 1 indicates a case where the number of cells to be encapsulated in droplet is one, 2 indicates a case where the number of cells to be encapsulated in droplet is two, and m indicates a case where the number of cells to be encapsulated in droplet is three or more.

FIG. 7 is a graph showing a ratio of the number of cells encapsulated in droplets according to the bead concentration in the microfluidic device according to an embodiment of the present disclosure, as compared to the existing system, wherein p indicates the existing system, o indicates the system according to an embodiment of the present disclosure, 1 indicates a case where the number of cells to be encapsulated in droplet is one, 2 indicates a case where the number of cells to be encapsulated in droplet is two, and m indicates a case where the number of cells to be encapsulated in droplet is three or more.

As shown in FIG. 7, it was confirmed that, when beads were introduced at a concentration of 1,500 beads/ul, the ratio at which two cells in droplet were encapsulated in the existing system was 20% or more, and the ratio at which three or more cells in droplet were encapsulated was about 5%. Meanwhile, it was confirmed that, when the bead concentration was 1,500 beads/ul, the ratio at which two cells in droplet were encapsulated in the system according to an embodiment of the present disclosure was about 1% or less.

(3) Optimization of Flow Rates for Droplet Generation

For accurate and high-throughput droplet sequencing, a high frequency of droplet generation and encapsulation of beads were prerequisites. The encapsulation was achieved by synchronization of the bead inlet with the droplet generation. For optimization of flow rates for droplet generation, two aqueous phases, Qw, were varied. No cells and beads were included in the aqueous phases, and the flow rates of the aqueous phases were set to Qw/2. Meanwhile, a rate of discharge of the carrier oil, Qo, was set to 12 ml/h.

Figure 8A:
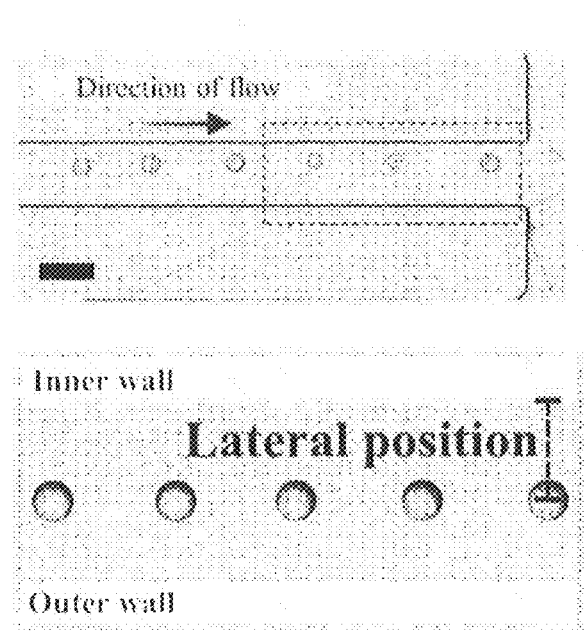
FIG. 8A is a diagram showing a lateral position in a spiral channel according to an embodiment.

When the beads travel through the spiral channel at a sufficient flow rate, the inertial and secondary flow act together on the beads for them to laterally migrate into a single focusing position. Here, the single focusing position lies near the inner wall because the drag force originated from the Dean flow guides the beads toward the inner wall. In addition, the inertial effect and parabolic flow field longitudinally arrange the focused beads with even spacing, as shown in FIG. 8A. Higher inertia is imparted by increasing the flow rate, thereby enhancing focusing and ordering. In this regard, the influence of the flow rate on inertial focusing with a lateral position was investigated. The flow rate varied in the range of 1.6 mL to 3.2 mL and the lateral positions of 300 beads from the inner wall at the end of the spiral channel were measured for each flow rate. Here, the bead concentration was set to 500 beads per µl for all conditions, and the results are shown in FIG. 8B.

FIG. 8A is a diagram showing the lateral position in the spiral channel according to an embodiment.

Figure 8B:
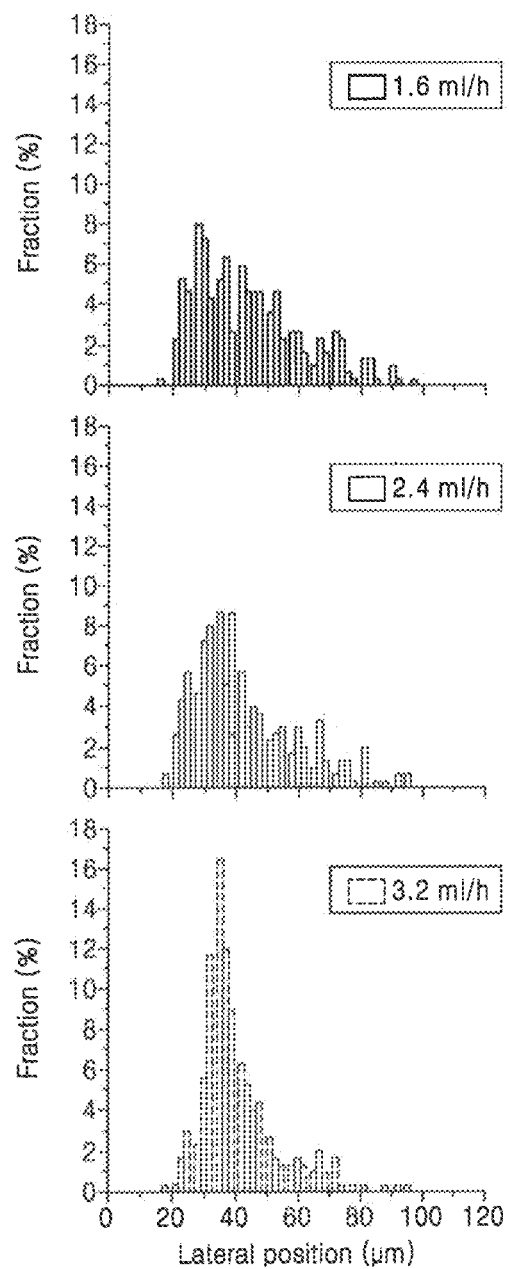
FIG. 8B is a graph showing bead distribution along the length of the lateral position in the spiral channel according to an embodiment.

FIG. 8B is a graph showing the bead distribution along the length of the lateral position in the spiral channel according to an embodiment.

As shown in FIG. 8B, the fraction distribution had a kurtosis of 2.85 at a flow rate of 1.6 mL/h. As the flow rate increased to 2.4 mL/h, beads were focused and the kurtosis was increased to 3.39. At a flow rate of 3.2 mL/h, a lateral position showed an unimodal distribution with a kurtosis of 5.63. Based on these results, it was confirmed that the flow rate for the droplet generation was at least 1.6 mL/h or higher.

(4) Synchronization of Bead Entrance

To enhance the ratio of droplets containing a single bead, the frequency of droplet generation was adjusted while maintaining the flow rates at a Qw/2 of 3.2 mL and Qo of 12 mL. Although the beads form trains with even spacing at low concentration under the condition of finite inertia, the separation between two following beads is very large, resulting in small bead-free droplets. As the bead concentration increases, the average number of beads in each train increases and the separation decreases. In addition, the inter-bead distance in each train decreases, thereby increasing the bead insertion frequency. Therefore, when the bead-entering frequency exceeds the drop-generation frequency at a very high concentration of beads, droplets containing multiple beads are produced, causing intermittent errors in cell indexing. That is, the cells encapsulated with multiple beads result in intermittent errors as mRNAs of a single cell are distributed to several beads. Therefore, it was intended to maximize the fraction of droplets containing a single bead (1B) and minimize the fraction of droplets containing multiple beads (mB). For this, the bead concentration varied in a range of 100 beads per µL to 1,250 beads per µL, and 1B and mB were measured from droplets collected from the outlet. The results are shown in FIG. 9B. An example of the collected droplets is shown in FIG. 9A.

Figure 9A:
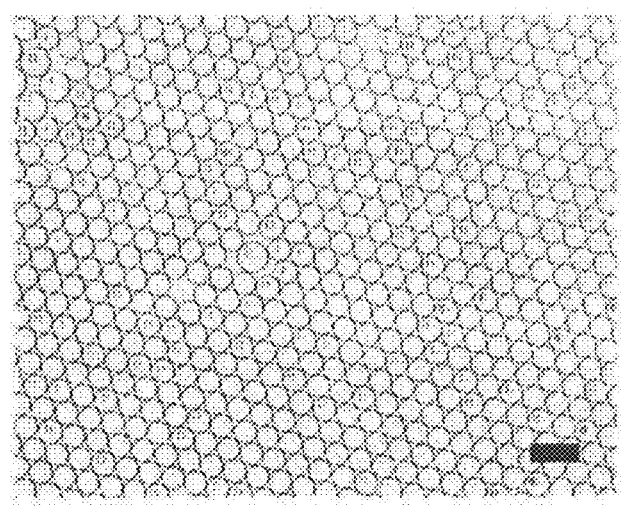
FIG. 9A is an optical microscope image showing droplets collected by using a microfluidic device according to an embodiment, wherein a scale bar herein is 200 um.
Figure 9B:
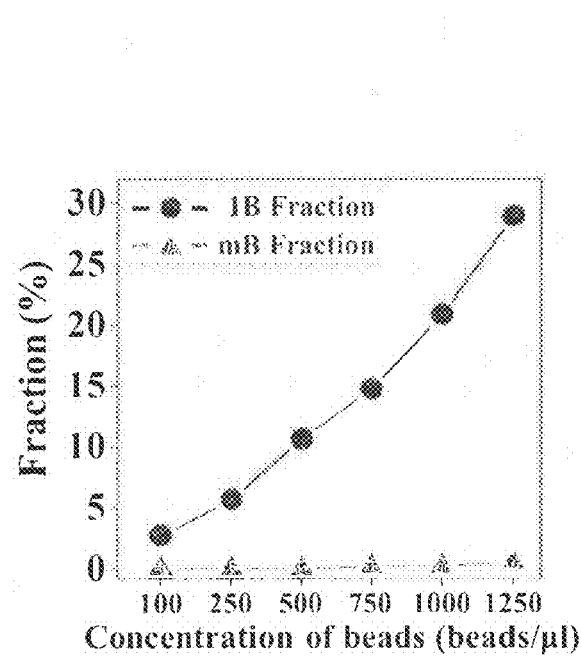
FIG. 9B is a graph showing fraction (%) of droplets containing a single bead and droplets containing multiple beads collected according to the bead concentration by using a microfluidic device according to an embodiment.

FIG. 9A is an optical microscope image showing the droplets collected by using the microfluidic device according to an embodiment, wherein a scale bar herein is 200 um.

FIG. 9B is a graph showing the fractions (%) of droplets containing a single bead and droplets containing multiple beads collected according to the bead concentration by using the microfluidic device according to an embodiment.

As shown in FIG. 9B, 1B increased from 3% to 28% with concentration, whereas mB remained equal to or lower than 0.5% at all concentrations. The small values of mB indicate that beads were well-aligned over the range of concentrations and the bead entering frequency did not exceed the drop-generation frequency, even at a high concentration of 1,250 beads per µL.

(5) Co-Encapsulation of Cell and Bead

To evaluate the co-encapsulation performance, cells and beads were simultaneously encapsulated. While encapsulating the cells, the influence of the bead concentration was analyzed in detail. The cell yield, defined as the fraction of cells encapsulated one-to-one with a bead for all cells, was estimated from images of collected droplets. The throughput, defined as the number of droplets containing one cell and one bead produced in a given period, was calculated as a product of the fraction of droplets containing one cell and one bead for all droplets and droplet-generation frequency. In addition, the results of the encapsulation of the one bead and the one cell in the one droplet in the microfluidic device according to an embodiment and the existing microfluidic device are shown in FIGS. 10B and 10C, respectively.

Figure 10A:
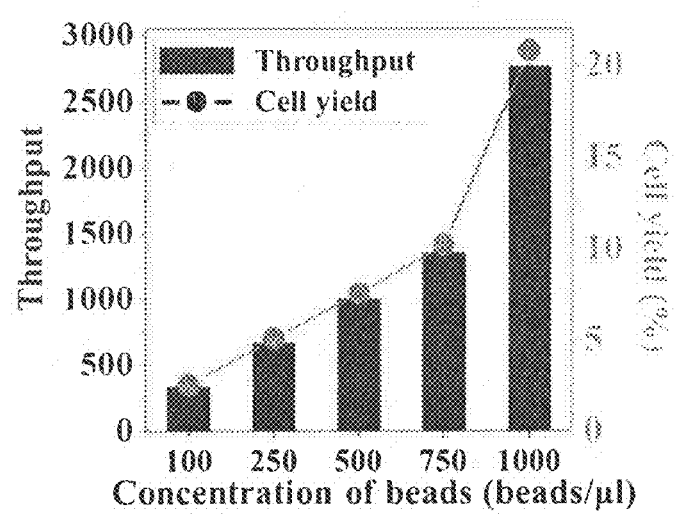
FIG. 10A is a graph showing a throughput and a cell yield according to the bead concentration in a microfluidic device according to an embodiment.

FIG. 10A is a graph showing the throughput and the cell yield according to the bead concentration in the microfluidic device according to an embodiment.

Figure 10B:
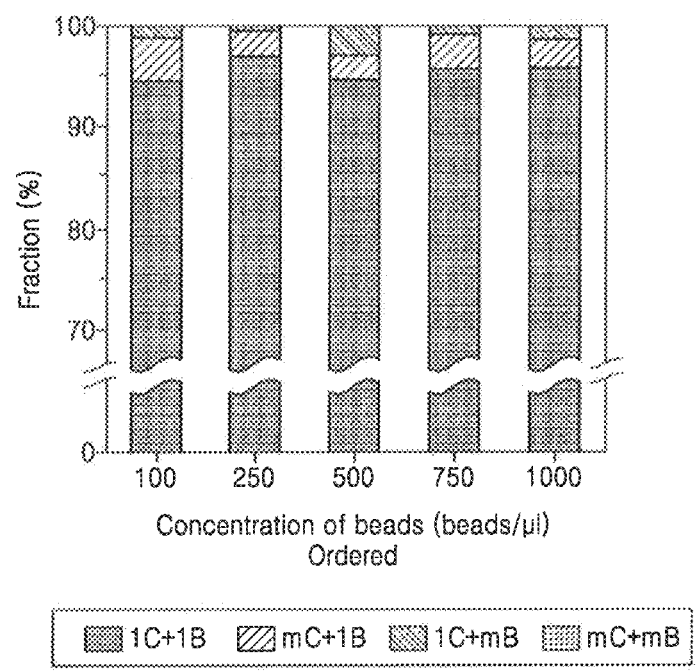
FIG. 10B is a graph showing fraction of droplets containing a single cell and a single bead according to the bead concentration in a microfluidic device according to an embodiment.

FIG. 10B is a graph showing the fraction of droplets containing a single cell and a single bead according to the bead concentration in the microfluidic device according to an embodiment.

Figure 10C:
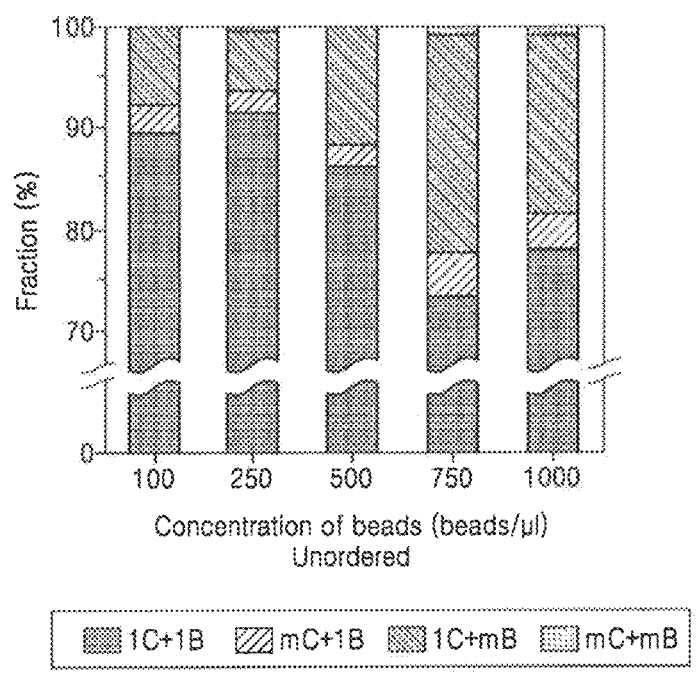
FIG. 10C is a graph showing fraction of droplets containing a single cell and a single bead according to the bead concentration in a microfluidic device according to an embodiment.

FIG. 10C is a graph showing the fraction of droplets containing a single cell and a single bead according to the bead concentration in the microfluidic device according to an embodiment.

As shown in FIG. 10A, it was confirmed that both the throughput and the cell yield increased along with the bead concentration. At a concentration of 1,000 beads per µL, the throughput and cell yield is 2,700 cells per min and 20%, respectively, which are much higher than the values of 300 cells per min and 3% with 100 beads per µL. This implies that 20%, which is higher than the existing device, of input cells are able to be co-encapsulated with a bead. These large values are ascribed to the high fraction of one-bead-in-droplet achieved by the encapsulation according to an embodiment. Based on the increased probability that a cell meets a bead, the probability of cell encapsulation with a bead can consequentially be increased.

In addition, as shown in FIGS. 10B and 10C, the fractions of droplets containing one cell and one bead (1C+1B), multiple cells and one bead (mC+1B), one cell and multiple beads (1C+mB), and multiple cells and multiple beads (mC+mB) are analyzed, and as a result, 1C+1B was as high as 95% and the sum of 1C+mB and mC+mB was as low as 2% over the entire range of bead concentrations in the microfluidic device according to an embodiment. The droplets containing multiple beads are found to appear at a very low ratio even at high bead concentration, referring that the microfluidic device according to an embodiment is beneficial for single-cell analysis, compared to a platform of the existing microfluidic device. In addition, errors in cell indexing can be reduced by maintaining a low fraction of multiple-beads-in-droplets. In particular, 1C+mB substantially increased up to 20% as shown in FIG. 10C. The results imply that the encapsulation in the microfluidic device according to an embodiment maximized the fraction of one bead-in-droplets while minimizing the fractions of empty droplets and multiple-beads-in-droplets. Therefore, a large fraction of encapsulated single cells was captured with a single bead, Increasing the cell yield while decreasing errors in cell indexing, making the microfluidic device according to an embodiment suitable for high throughput single-cell analysis.

(6) Single Cell RNA Sequencing

To validate and investigate the performance of the microfluidic device according to an embodiment, a cell suspension of HEK293T and NIH3T3 cells was injected at 250 cells per µL, and a barcoded bead suspension was injected at 1,000 beads per µL into the device. After encapsulation, mixing, cell lysis, and mRNA capture, droplets were collected for 2.5 minutes from the outlet. Then, beads collected from the droplets were subjected to reverse transcription, amplification, library preparation, and sequencing.

To evaluate the appositeness of barcodes, the nucleotide ratio of the cell index and molecular index of read 1 was calculated. From the sequencing data set, 2,165 cells (over 686 UMIs per cell) in the existing microfluidic device and 1,719 cells (over 702 UMIs per cell) in the microfluidic device according to an embodiment were collected based on the cumulative fraction of UMIs curves. Among the selected cells, 229 cells in the existing microfluidic device and 282 cells in the microfluidic device according to an embodiment were discarded as low-quality cells. Afterwards, density plot analysis was performed on the UMIs per cell, and the results are shown in FIG. 11.

Figure 11A:
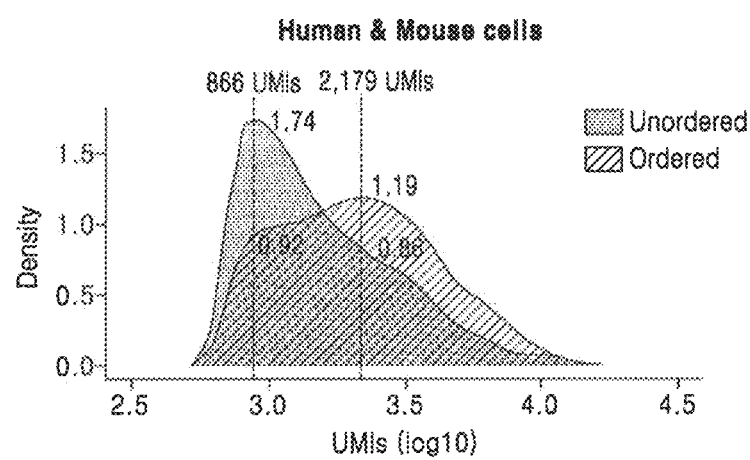
FIG. 11A is a graph showing a density plot of UMIs per cell of combined human and mouse cells according to the existing microfluidic device (Unordered) and the microfluidic device according to an embodiment (Ordered).

FIG. 11A is a graph showing the density plot of UMIs per cell of combined human and mouse cells according to the existing microfluidic device (Unordered) and the microfluidic device according to an embodiment (Ordered).

Figure 11B:
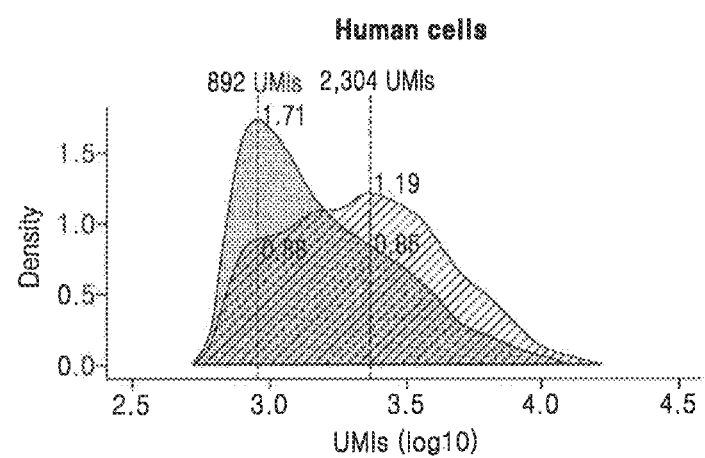
FIG. 11B is a graph showing a density plot of UMIs per cell of only human cells according to the existing microfluidic device (Unordered) and the microfluidic device according to an embodiment (Ordered).
Figure 11C:
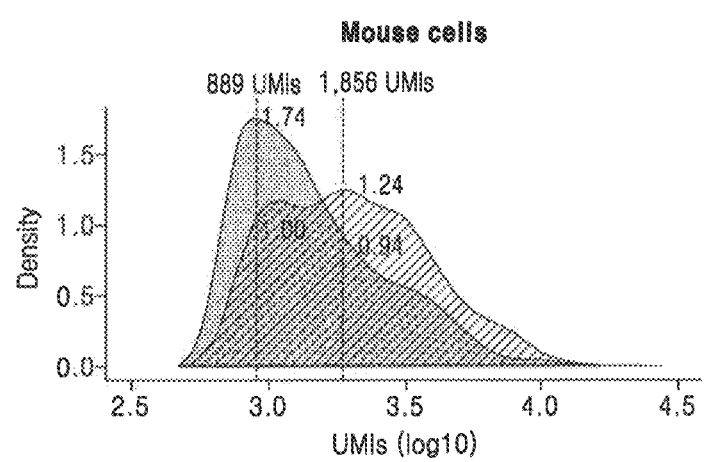
FIG. 11C is a graph showing a density plot of UMIs per cell of only mouse cells according to an existing microfluidic device (Unordered) and a microfluidic device according to an embodiment (Ordered).

FIG. 11B is a graph showing density plot of UMIs per cell of only human cells according to the existing microfluidic device (Unordered) and the microfluidic device according to an embodiment (Ordered).

FIG. 11B is a graph showing the density plot of UMIs per cell of only human cells in the existing microfluidic device (Unordered) and the microfluidic device according to an embodiment (Ordered).

As shown in FIG. 11, when human and mouse cells were analyzed together, the number of UMIs at the top peak in the microfluidic device according to an embodiment was 2,179, whereas that of the existing microfluidic device was 866, which is less than half, and a similar pattern was observed for human cells only and mouse cells only. When two beads are encapsulated with one cell, the transcript number was halved because mRNA fragments were divided into two for capture by two barcoded beads. In addition, the number of cells was duplicated as two barcoded beads were sequenced individually. The results of FIG. 11 indicate that bead doublets generated by the encapsulation in the existing microfluidic device significantly reduce the quality of single-cell sequencing data by underestimating the transcript number and overestimating the cell number. In addition, the results of FIG. 11 also indicate that inaccurate transcript and cell numbers caused by bead doublet-mediated barcoding error can mislead the single-cell mRNA profile.

Meanwhile, it was confirmed that the encapsulation in the microfluidic device according to an embodiment enable high-throughput barcoding and while minimizing barcoding errors.

Referring to the results above, it was confirmed that the existing system increased the probability of entering two or more clusters with the increased concentrations of the cell and the bead, and when the concentrations of the cell and the bead decreased, the cell and the bead were less likely to meet to form droplets, resulting in lower efficiency (yield). Meanwhile, it was also confirmed that the system according to an embodiment formed droplets by the inertial ordering of the cells or the beads, thereby simultaneously improving two conflicting parameters described above and minimizing the barcoding erros.

The invention claimed is:

1. A method of forming droplets for single-cell analysis, the method comprising:
providing cells;
providing one or more distinctly barcoded RNA capture beads;
providing one or more oil phase;
encapsulating in one droplet a single cell of the cells and a single bead of the one or more distinctly barcoded RNA capture beads; and
mixing the cells and beads encapsulated in the droplet,
wherein the providing of the cells or the providing of the one or more distinctly barcoded RNA capture beads is provided through inertial ordering before the single cell or the single bead are encapsulated in the one droplet, and
wherein the inertial ordering occurs through a spiral channel of a microfluidic device to which the cells or the one or more distinctly barcoded RNA capture beads are provided,
wherein the oil phase in the providing one or more oil phase step has a flow rate in a range of 4.0 mL/h to 8.0 mL/h, and
wherein the cells in the providing cells step and beads in the providing one or more distinctly barcoded RNA capture beads step have a flow rate in a range of 8.0 mL/h to 14 mL/h 6.0 mL/h.

2. The method of claim 1, wherein the one or more distinctly barcoded RNA capture beads are provided with a cell lysate.

3. The method of claim 1, wherein the one or more distinctly barcoded RNA capture beads include multiple nucleotides or oligonucleotides, each molecularly barcoded on a surface of the one or more distinctly barcoded RNA capture beads.

4. The method of claim 3, wherein the multiple nucleotides or oligonucleotides include a nucleotide sequence for capture of mRNAs in the single cell.

5. The method of claim 3, wherein a sequence the multiple nucleotides or oligonucleotides includes an oligo-dT sequence or a primer sequence.

* * * * *